United States Patent
Hirata

(10) Patent No.: US 7,439,036 B2
(45) Date of Patent: Oct. 21, 2008

(54) PROCESS FOR PRODUCING OPTICALLY ACTIVE OCTAHYDRO-1H-INDOLE-2-CARBOXYLIC ACID

(75) Inventor: Norihiko Hirata, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 319 days.

(21) Appl. No.: 10/975,076

(22) Filed: Oct. 28, 2004

(65) Prior Publication Data

US 2005/0106690 A1    May 19, 2005

(30) Foreign Application Priority Data

Oct. 30, 2003    (JP)    ............... 2003-370251

(51) Int. Cl.
*C12P 1/00*    (2006.01)
(52) U.S. Cl. ............... 435/41; 435/107; 548/492
(58) Field of Classification Search ............... 435/41, 435/107; 548/492
See application file for complete search history.

(56) References Cited

U.S. PATENT DOCUMENTS

| | | | |
|---|---|---|---|
| 4,868,307 A | 9/1989 | Barton et al. | |
| 4,898,822 A | 2/1990 | Asada et al. | |
| 5,015,641 A | 5/1991 | Andrews et al. | |
| 6,372,470 B1 | 4/2002 | Hourai et al. | |
| 6,518,053 B2 | 2/2003 | Hourai et al. | |

FOREIGN PATENT DOCUMENTS

| | | |
|---|---|---|
| EP | 0 969 094 A2 | 1/2000 |
| EP | 0 974 670 A2 | 1/2000 |
| EP | 1 323 729 A1 | 7/2003 |
| JP | 7-163364 A | 6/1995 |
| JP | 7-213280 A | 8/1995 |
| JP | 2 550 369 B2 | 8/1996 |
| JP | 2000-78988 A | 3/2000 |

OTHER PUBLICATIONS

C.J. Blankley et al., "Synthesis and Structure—Activity Relationships of Potent New Angiotensin Converting Enzyme Inhibitors Containing Saturated Bicylic Amino Acids", *J. Med. Chem.*, vol. 30, 1987, pp. 992-998.

M. Vincent et al., "Stereoselective Synthesis of a New Perhydroindole Derivative of Chiral Iminodiacid, a Potent Inhibitor of Angiotensin Converting Enzyme", *Tetrahedron Letters*, vol. 23, No. 16, 1982, pp. 1677-1680.

Michael Vincent et al., "Synthesis and Ace Inhibitory Activity of the Stereoisomers of Perindopril (S 9490) and Perindoprilate (S 9780)", *Drug Design Discovery*, vol. 9, 1992, pp. 11-28.

*Primary Examiner*—Leon B. Lankford, Jr.
*Assistant Examiner*—Susan E. Fernandez
(74) *Attorney, Agent, or Firm*—Foley & Lardner LLP

(57) ABSTRACT

To provide an enzymatic resolution process for efficiently producing an optically active N-protected-octahydro-1H-indole-2-carboxylic acid denoted by the formula (2):

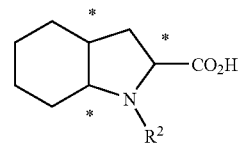

(2)

by using an enzyme capable of asymmetrically hydrolyzing the —$CO_2R^1$ group in the formula (1)

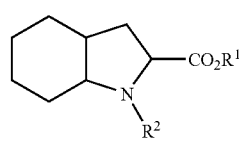

(1)

wherein $R^1$ indicates an alkyl group having a carbon number of 1 to 4, $R^2$ indicates a protecting group of the imino group, and the carbon atoms marked with asterisks (*) indicate asymmetrical carbon atoms.

9 Claims, No Drawings

PROCESS FOR PRODUCING OPTICALLY ACTIVE OCTAHYDRO-1H-INDOLE-2-CARBOXYLIC ACID

BACKGROUND OF THE INVENTION

Field of the Invention

The present invention relates to an enzymatic resolution process for producing an optically active N-protected-octahydro-1H-indole-2-carboxylic acid, which is a useful intermediate compound for producing pharmaceuticals such as an Angiotensin-converting enzyme inhibitor, or a Bradykinin antagonist.

For the production of an optically active N-protected-octahydro-1H-indole-2-carboxylic acid, there are known (i) processes using optically active amino acids as a starting material and (ii) processes of optical resolution of indoline-2-carboxylic acid or an octahydro-1H-indole-2-carboxylic acid or derivatives thereof, which are produced from an indole-2-carboxylic acid as a starting material.

Said processes under item (i) above are a method of using a β-iodoalanine derivative and adipic anhydride as the starting materials as described in the claims of EP No. 1323729 (A1), a method of using an asparaginic acid derivative and 3-bromocyclohexene as the starting materials as described in Example 1 of Japanese Patent No. 2550369, and the like.

In addition, the processes illustrated under item (ii) above are a method of optically resolving ethyl octahydro-1H-indole-2-carboxylate, which is produced by reducing ethyl indole-2-carboxylate, with 10-camphasulfonic acid as described in Preparation Example 4, of U.S. Pat. No. 5,015,641, a method of optically resolving a tert-butyl octahydro-1H-indole-2-carboxylate with tartaric acid (p. 997 J. of Medicinal Chemistry, 30 (6), 992-998, (1987)), a method of optically resolving an N-benzoiloctahydro-1H-indole-2-carboxylic acid with α-methylbenzylamine as disclosed in p. 997 J. of Medicinal Chemistry, 30 (6), 992-998, (1987), a method of optically resolving an indoline-2-carboxylic acid prepared from an indole-2-carboxylic acid with α-methylbenzylamine, and subsequently reducing the resolved product to produce an octahydro-2-indolecarboxylic acid as disclosed p. 1678, Tetrahedron Letters., 23(16), 1677-1680, (1982), and the like.

However, the processes using, as the starting material, an optical active amino acid under item (i) above have problems in that they require many steps, and expensive reaction reagents. Moreover, the optical resolution methods under item (ii) above also have problems in that resolution efficiency is insufficient, and further recrystallization is required after the optical resolution.

A process of using an enzyme for producing an optically active octahydro-1H-indole-2-carboxylic acid or an N-protected species thereof by hydrolyzing an octahydro-1H-indole-2-carboxylate or an N-protected compound thereof is not known.

According to the present invention, an optically active N-protected-octahydro-1H-indole-2-carboxylic acid can be efficiently produced.

The present invention provides a process for producing an optically active N-protected-octahydro-1H-indole-2-carboxylic acid of formula (2):

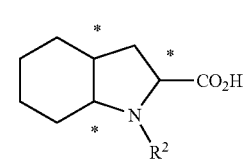

(2)

wherein $R^2$ represents a protecting group of an imino group, and the carbon atoms denoted with asterisks (*) represent asymmetric carbon atoms, which process comprises reacting a mixture of enantiomers of N-protected-octahydro-1H-indole-2-carboxylate of formula (1):

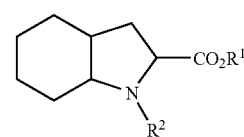

(1)

wherein $R^1$ is a C1-4 alkyl group, and $R^2$ is as defined above, with an enzyme capable of asymmetrically hydrolyzing the $-CO_2R^1$ group of formula (1), wherein the enzyme is an enzyme i) produced by a microorganism deposited with accession number FERM BP-6703 or a mutant thereof, ii) comprising a polypeptide sequence of SEQ ID NO:1, or iii) comprising a polypeptide sequence of SEQ ID NO:1 modified by deletion, substitution or both of at least one amino acid.

DETAILED DESCRIPTION OF THE INVENTION

Hereinafter, the present invention will be set forth in detail.

N-protected-octahydro-1H-indole-2-carboxylate of formula (1) is explained first. The C1-4 alkyl group represented by $R^1$ includes, for example, a methyl group, an ethyl group, an n-propyl group, an isopropyl group, an n-butyl group, an isobutyl group, a sec-butyl group, and a tert-butyl group.

The protecting groups of the imino group represented by $R^2$ include, for example, alkoxycarbonyl groups such as a tert-butoxycarbonyl group, arylalkyloxycarbonyl groups such as a benzyloxycarbonyl group, a p-methoxybenzyloxycarbonyl group and a p-nitrobenzyloxycarbonyl group, allyloxy and alkoxycarbonyl groups such as an allyloxycarbonyl group and a 9-fluorenylmethoxycarbonyl group, acyl groups such as an acetyl group and a benzoyl group, substituted alkyl groups such as a benzyl group, and the like.

Preferred $R^2$ groups are a tert-butoxycarbonyl group, a benzyloxycarbonyl group, an acetyl group, a benzoyl group and benzyl group, and more preferred is a benzyloxycarbonyl group, which can be readily deprotected to derivatize the protected compounds, for example, to intermediate compounds for the production of the Angiotensin-converting enzyme inhibitor or Bradykinin antagonist.

The N-protected-octahydro-1H-indole-2-carboxylic acid ester to be resolved, hereinafter referred to also as "substrate", can be produced, e.g., in accordance with the method described in Journal of Medicinal Chemistry, 30 (6), 992, (1987), by catalytic hydrogenation to reduce an indole-2-carboxylate, and subsequently protecting the imino group of the obtained octahydro-1H-indole-2-carboxylate by a known manner or by a similar manner as described in Drug Design and Discovery (1992), 9(1), 11-28.

The substrate that was produced by a method other than the above-described method may also be used.

Examples of the substrate include, for example,
methyl N-tert-butoxycarbonyloctahydro-1H-indole-2-carboxylate,
ethyl N-tert-butoxycarbonyloctahydro-1H-indole-2-carboxylate,
n-propyl N-tert-butoxycarbonyloctahydro-1H-indole-2-carboxylate,
isopropyl N-tert-butoxycarbonyloctahydro-1H-indole-2-carboxylate,
n-butyl N-tert-butoxycarbonyloctahydro-1H-indole-2-carboxylate,
isobutyl N-tert-butoxycarbonyloctahydro-1H-indole-2-carboxylate,
sec-butyl N-tert-butoxycarbonyloctahydro-1H-indole-2-carboxylate,
tert-butyl N-tert-butoxycarbonyloctahydro-1H-indole-2-carboxylate,
methyl N-benzyloxycarbonyloctahydro-1H-indole-2-carboxylate,
ethyl N-benzyloxycarbonyloctahydro-1H-indole-2-carboxylate,
n-propyl N-benzyloxycarbonyloctahydro-1H-indole-2-carboxylate,
isopropyl N-benzyloxycarbonyloctahydro-1H-indole-2-carboxylate,
n-butyl N-benzyloxycarbonyloctahydro-1H-indole-2-carboxylate,
isobutyl N-benzyloxycarbonyloctahydro-1H-indole-2-carboxylate,
sec-butyl N-benzyloxycarbonyloctahydro-1H-indole-2-carboxylate,
tert-butyl N-benzyloxycarbonyloctahydro-1H-indole-2-carboxylate,
methyl N-p-methoxybenzyloxycarbonyloctahydro-1H-indole-2-carboxylate,
ethyl N-p-methoxybenzyloxycarbonyloctahydro-1H-indole-2-carboxylate,
n-propyl N-p-methoxybenzyloxycarbonyloctahydro-1H-indole-2-carboxylate,
isopropyl N-p-methoxybenzyloxycarbonyloctahydro-1H-indole-2-carboxylate,
n-butyl N-p-methoxybenzyloxycarbonyloctahydro-1H-indole-2-carboxylate,
isobutyl N-p-methoxybenzyloxycarbonyloctahydro-1H-indole-2-carboxylate,
sec-butyl N-p-methoxybenzyloxycarbonyloctahydro-1H-indole-2-carboxylate,
tert-butyl N-p-methoxybenzyloxycarbonyloctahydro-1H-indole-2-carboxylate,
methyl N-p-nitrobenzyloxycarbonyloctahydro-1H-indole-2-carboxylate,
ethyl N-p-nitrobenzyloxycarbonyloctahydro-1H-indole-2-carboxylate,
n-propyl N-p-nitrobenzyloxycarbonyloctahydro-1H-indole-2-carboxylate,
isopropyl N-p-nitrobenzyloxycarbonyloctahydro-1H-indole-2-carboxylate,
n-butyl N-p-nitrobenzyloxycarbonyloctahydro-1H-indole-2-carboxylate,
isobutyl N-p-nitrobenzyloxycarbonyloctahydro-1H-indole-2-carboxylate,
sec-butyl N-p-nitrobenzyloxycarbonyloctahydro-1H-indole-2-carboxylate,
tert-butyl N-p-nitrobenzyloxycarbonyloctahydro-1H-indole-2-carboxylate,
methyl N-allyloxycarbonyloctahydro-1H-indole-2-carboxylate,
ethyl N-allyloxycarbonyloctahydro-1H-indole-2-carboxylate,
n-propyl N-allyloxycarbonyloctahydro-1H-indole-2-carboxylate,
isopropyl N-allyloxycarbonyloctahydro-1H-indole-2-carboxylate,
n-butyl N-allyloxycarbonyloctahydro-1H-indole-2-carboxylate,
isobutyl N-allyloxycarbonyloctahydro-1H-indole-2-carboxylate,
sec-butyl N-allyloxycarbonyloctahydro-1H-indole-2-carboxylate,
tert-butyl N-allyloxycarbonyloctahydro-1H-indole-2-carboxylate,
methyl N-9-fluorenylmethoxycarbonyloctahydro-1H-indole-2-carboxylate,
ethyl N-9-fluorenylmethoxycarbonyloctahydro-1H-indole-2-carboxylate,
n-propyl N-9-fluorenylmethoxycarbonyloctahydro-1H-indole-2-carboxylate,
isopropyl N-9-fluorenylmethoxycarbonyloctahydro-1H-indole-2-carboxylate,
n-butyl N-9-fluorenylmethoxycarbonyloctahydro-1H-indole-2-carboxylate,
isobutyl N-9-fluorenylmethoxycarbonyloctahydro-1H-indole-2-carboxylate,
sec-butyl N-9-fluorenylmethoxycarbonyloctahydro-1H-indole-2-carboxylate,
tert-butyl N-9-fluorenylmethoxycarbonyloctahydro-1H-indole-2-carboxylate,
methyl N-acetyloctahydro-1H-indole-2-carboxylate,
ethyl N-acetyloctahydro-1H-indole-2-carboxylate,
n-propyl N-acetyloctahydro-1H-indole-2-carboxylate,
isopropyl N-acetyloctahydro-1H-indole-2-carboxylate,
n-butyl N-acetyloctahydro-1H-indole-2-carboxylate,
isobutyl N-acetyloctahydro-1H-indole-2-carboxylate,
sec-butyl N-acetyloctahydro-1H-indole-2-carboxylate,
tert-butyl N-acetyloctahydro-1H-indole-2-carboxylate,
methyl N-benzoyloctahydro-1H-indole-2-carboxylate,
ethyl N-benzoyloctahydro-1H-indole-2-carboxylate,
n-propyl N-benzoyloctahydro-1H-indole-2-carboxylate,
isopropyl N-benzoyloctahydro-1H-indole-2-carboxylate,
n-butyl N-benzoyloctahydro-1H-indole-2-carboxylate,
isobutyl N-benzoyloctahydro-1H-indole-2-carboxylate,
sec-butyl N-benzoyloctahydro-1H-indole-2-carboxylate,
tert-butyl N-benzoyloctahydro-1H-indole-2-carboxylate,
methyl N-benzyloctahydro-1H-indole-2-carboxylate,
ethyl N-benzyloctahydro-1H-indole-2-carboxylate,
n-propyl N-benzyloctahydro-1H-indole-2-carboxylate,
isopropyl N-benzyloctahydro-1H-indole-2-carboxylate,
n-butyl N-benzyloctahydro-1H-indole-2-carboxylate,
isobutyl N-benzyloctahydro-1H-indole-2-carboxylate,
sec-butyl N-benzyloctahydro-1H-indole-2-carboxylate,
tert-butyl N-benzyloctahydro-1H-indole-2-carboxylate, and the like.

The substrate may be a mixture of eight optical isomers, which mixture is typically a racemic mixture, or may be a mixture of a single optical isomer and an antipode thereof. Preferred is the mixture of a single optical isomer and an antipode thereof.

More preferred is a mixture of the compound of formula (1') and the antipode thereof of formula (1").

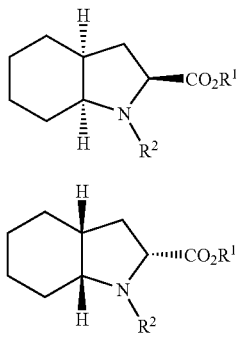

wherein R¹ and R² are as defined above.

The enzymes capable of asymmetrical hydrolyzing the substrate to produce an optically active N-protected-octahydro-1H-indole-2-carboxylic acid include, for example, a hydrolase including esterase and lipase, originated from a microorganism *Chromobacterium* SC-YM-1 strain(FERM BP-6703) or a mutant thereof.

The enzymes may be, for example, an enzyme derived from a mutant produced from the aforementioned microorganism by treatment such as a mutation agent or ultraviolet rays, an enzyme produced by a recombinant microorganism transformed by introducing the gene encoding the present enzyme, and a mutant enzyme produced by addition, substitution or deletion of at least one amino acid in the amino acid sequence of the enzyme by means of the genetic engineering method.

The recombinant microorganisms can be prepared by introducing genes encoding the enzymes, for example, in accordance with the genetic engineering processes described in, e.g., Molecular Cloning 2nd edition, written by J. Sambrook, E. F. Fritsch, and T. Maniatis, Cold Spring Harbor Laboratory, published in 1989, etc.

More specifically, the enzymes can be prepared in a similar manner as described in Japanese Unexamined Patent Application Publication No. 7-163364.

The mutant enzyme can be prepared by genetic engineering process, for example, of Olfert Landt et al. (Gene 96 125-128 1990). More specifically, the mutant enzymes can be prepared as described in Japanese Unexamined Patent Application Publication Nos. 2000-78988 and 7-213280.

Examples of the mutant enzyme that can be prepared in this manner include, for example, a mutant esterase prepared from an esterase derived from *Chromobacterium* SC-YM-1 strain, and specific examples thereof include, for example, an enzyme having amino acid substitution(s) or deletion or both in the amino acid of SEQ ID NO: 1. Examples of the substitution(s) or deletion or both are denoted by 160A, 160I, 160L, 160S, 160V, 189A, 189F, 189H, 189I, 189L, 189R, 189S, 189T, 189V, 189Y, 160A189F363term, 160A189H363term, 160A189Y363term, 160S189F363term or 160S189H363term, which notations mean that the 160th and/or 189th amino acids, which are glycine in SEQ ID NO:1, are substituted with the amino acid A, I, L, V, F, H, R, S, T or Y in SEQ ID NO:1 and 363term means that the polypeptide is terminated at the 363rd position and consists of the 1st to 362nd amino acids in SEQ ID NO 1. For example, 160A189Y363term means an enzyme having alanine at 160th position and tyrosine at 189th position in place of glycine in SEQ ID NO:1 and deletion of 8 C-terminal amino acids in SEQ ID NO:1.

The microorganism capable of producing the enzyme can be liquid cultivated by a known manner. Various medium containing, as required, carbon sources, nitrogen sources, inorganic substances and the like can be used for the cultivating microorganisms.

For instance, the carbon sources include glucose, glycerin, an organic acid, honey, and the like. The nitrogen sources include a peptone, yeast extract, malt extract, a soybean powder, a corn steep linker, a cottonseed powder, dry yeast, casamino acids, ammonium chloride, ammonium nitrate, ammonium sulfate, urea, and the like.

The inorganic substances include hydrochlorides of metals such as potassium, sodium, magnesium, iron, manganese, cobalt, zinc, and the like; sulfates of metals mentioned above; phosphates of the aforementioned metals; and the like. More specifically, the salts that may be used include potassium chloride, sodium chloride, magnesium sulfate, ferrous sulfate, manganese sulfate, cobalt chloride, zinc sulfate, potassium phosphate, sodium phosphate, and the like.

In addition, triglycerides such as olive oil or tributyrin, or the above-mentioned substrate may be added to the medium to enhance the capability of the microorganism capable of asymmetrically hydrolyzing the ester of formula (1).

The cultivation is suitably carried out under an aerobic atmosphere, and preferred are the shake cultivation or the aeration shake cultivation. The cultivation temperature is normally from about 20 to about 40° C., preferably from about 25 to 35° C. The pH is preferably from about 6 to about 8. The cultivation time may vary depending on various conditions, but is preferably from about 1 day to 7 days.

Solid cultivation method may also be used to obtain a microorganism cells capable of asymmetrical hydrolyzing the above-described substrate.

The enzyme can be purified by a suitable method as usually used in the purification of enzymes. For instance, the cultivated cells of the microorganisms are first disrupted by supersonic treatment, Dyno-Mill treatment or French press treatment. Then, after removal of insoluble materials from the disrupted mixture, the desired enzyme can be obtained by centrifugation or the like, and can be further purified by a suitable purification method such as cation ion exchange chromatography, anion ion exchange chromatography, hydrophobic column chromatography, or gel filtration column chromatography, or by a combination thereof normally employed for enzyme purification.

Examples of the carrier that may be used for such a column chromatography include, for example, DEAE-Sepharose fastflow (manufactured by Amersham Pharmacia Biotech, Inc.), Butyl-Toyopearl 650S (manufactured by Tosoh Co., Ltd.) and the like.

The enzyme can be used in various forms such as a purified enzyme, a crude enzyme, cultivated products of the microorganisms producing the enzyme, the cells of the microorganisms, treated products thereof, or the like. The aforementioned treated products stand for, for instance, a freeze-dried, acetone-dried, disrupted, autolysate, ultrasonically treated, extracted, or alkali-treated cells of the microorganism producing the enzyme. Furthermore, the enzyme with various purities or forms as mentioned above can be used after immobilization, for example, by means of a well-known method including absorption to inorganic carriers such as silica gel or ceramics, cellulose, or ion exchange resin, the polyacrylamide method, sulfur-containing polysaccharide gel methods such as the carrageenan gel method, the alginic acid gel method, the agar gel method, and the like.

The amount of the enzyme that may be used is suitably determined so as not to cause a delay of the reaction rate and reduction of selectivity. For instance, the purified enzyme or the crude enzyme is normally used in an amount of from about 0.001 to about 2 parts by weight, preferably from about 0.002 to 0.5 part by weight per one part by weight of the amount of the substrate.

Cultivated products of the microorganisms, cells of the microorganisms or treated products thereof is usually used in the amount of from about 0.01 to about 200 parts by weight and it is preferably from about 0.1 to 50 parts by weight per one part by weight of the above-described substrate.

Water may be added as an aqueous buffer in the asymmetrical hydrolysis reaction. The aqueous buffers include, for example, aqueous buffers of inorganic acid salts, and examples thereof include, for example, aqueous alkali metal phosphate solutions such as an aqueous sodium phosphate solution or an aqueous potassium phosphate solution, aqueous buffers of organic acid salts of alkali metal acetates such as an aqueous sodium acetate solution, or an aqueous potassium acetate solution, and the like.

The amount of the water that may be used normally ranges from 0.5 part by weight to 200 parts by weight per one part by weight of the substrate.

The asymmetrical hydrolysis reaction in the present invention may also be carried out in the presence of an organic solvent such as a hydrophobic organic solvent, a hydrophilic organic solvent, or the like.

The hydrophobic organic solvents include, for example, aliphatic ethers such as tert-butyl methyl ether or diisopropyl ether; hydrocarbons such as toluene, hexane, cyclohexane, heptane, octane or isooctane; and the like.

In addition, the hydrophilic organic solvents include, for example, alcohols such as tert-butanol, methanol, ethanol, isopropanol, isobutanol or n-butanol, alicyclic ethers such as tetrahydrofuran; sulfoxides such as dimethylsulfoxide; ketones such as acetone; nitrites such as acetonitrile; amides such as N,N-dimethylformamide, and the like.

These hydrophobic organic solvents and hydrophilic solvents are each used singly or as a mixture of two or more of them. A mixture of the hydrophobic organic solvent and the hydrophilic solvent may also be used.

The solvent is preferably used in the amount of 200 parts by weight or less, more preferably from 0.1 to 100 parts by weight per one part by weight of the substrate.

The asymmetrical hydrolysis reaction is carried out, for example, by mixing water, the substrate and the enzyme, or by mixing the organic solvent, water, the substrate, and the enzyme.

The pH of the reaction system is suitably set so that asymmetrical hydrolysis reaction selectively proceeds.

The pH of the reaction system is normally adjusted within a range of from about 4 to about 10, preferably from about 6 to about 8 by adding a base.

The bases that may be used include, for example, alkali metal hydroxides such as sodium hydroxide or potassium hydroxide, alkali metal carbonates such as sodium carbonate or potassium carbonate, alkali earth metal carbonates such as calcium carbonate, alkali metal bicarbonates such as sodium bicarbonate or potassium bicarbonate; phosphates such as sodium dihydrogenphosphate, disodium hydrogenphosphate, potassium dihydrogenphosphate, or dipotassium hydrogenphosphate, organic bases such as triethylamine or pyridine, ammonia, and the like. The base may be used solely, or in a mixture of two or more of them. The base is normally added as an aqueous solution, but may also be added as a mixture of an organic solvent and water. The same organic solvent as used in the reaction may also be used for this purpose. Furthermore, the base may be added as a solid, or as a suspension.

The reaction temperature normally ranges from about 5 to 65° C., preferably from about 20 to 50° C.

The reaction mixture containing the optically active N-protected-octahydro-1H-indole-2-carboxylic acid of formula (2), hereinafter referred to as asymmetrically hydrolyzed carboxylic acid or as optically active carboxylic acid, and the optically active N-protected-octahydro-1H-indole-2-carboxylic acid ester, which was not hydrolyzed, hereinafter referred to as a remaining ester(s) is obtained.

The optically active carboxylic acid and the remaining ester are usually separated from the reaction mixture, and also from the enzyme and buffer solution, and the optically active carboxylic acid and the remaining ester are usually separated each other by suitable after-treatment operations such as extraction, phase separation, and/or evaporation of the solvent and optionally silica gel column chromatography and the like.

An organic solvent miscible with both water and the hydrophobic organic solvent used in the reaction is typically removed by distillation prior to phase separation, if appropriate.

Insolubles that may be present in the reaction mixture such as the enzyme, an immobilizing carrier, and the like can be removed by filtration, if necessary.

The extraction and phase separation is typically conducted by adjusting the pH of the reaction mixture with a suitable acid or base within a range of from about 6 to about 12, preferably from about 7 to about 10.

The acids include, for example, inorganic acids such as hydrogen chloride, hydrogen bromide, sulfuric acid and phosphoric acid, acidic salts of inorganic acids thereof and metals, organic acids such as acetic acid, citric acid and methanesulfonic acid, and acidic salts of organic acids thereof and metals. The same bases as used in adjusting the pH of the hydrolysis reaction can also be used. The separation by extraction may be repeated a plurality of times, if necessary.

The residual ester remaining in the reaction mixture is usually extracted with a hydrophobic organic solvent followed by phase separation while separated water phase containing the asymmetrically hydrolyzed optically active carboxylic acid is obtained.

The hydrophobic organic solvents that may be used in the extraction above include, for example, aliphatic ethers such as tert-butylmethyl ether and isopropyl ether; hydrocarbons such as toluene, hexane, cyclohexane, heptane, octane or isooctane; halogenated hydrocarbons such as dichloromethane, dichloroethane, chloroform, chlorobenzene or o-dichlorobenzene: and esters such as methyl acetate, ethyl acetate, or butyl acetate.

The amount of the hydrophobic organic solvent that may be used is not particularly limited and is normally from 0.1 to 200 parts by weight, preferably from about 0.2 to about 100 parts by weight per one part by weight of the substrate.

Alternatively, the hydrophobic organic solvent used in the asymmetrical hydrolysis reaction may also serve as extraction solvent and the resulting reaction mixture is settled and separated into the organic phase and water phase without adding the hydrophibic organic solvent, or a suitable amount of the hydrophobic organic solvent for phase separation and extraction may be added.

The residual ester in the organic phase, which is separated from the optically active carboxylic acid can be isolated by removing the organic solvent of the organic phase by distillation. The isolated residual ester may be further purified by column chromatography or the like, if necessary.

The residual ester thus obtained can be further hydrolyzed with an alkali to produce the optically active N-protected-octahydro-1H-indole-2-carboxylic acid, which can be further purified by column chromatography, recrystallization, or the like, if necessary.

The optically active carboxylic acid produced by the asymmetrical hydrolysis is usually present in the separated water phase and is isolated from the water phase normally by adjusting the pH of the water phase with a suitable acid or base within a range from about 1 to about 6, preferably from about 2 to about 5, by extracting the optically active carboxylic acid with an hydrophobic organic solvent as used above for extracting the unreacted ester, and by phase separation typically followed by evaporation of the hydrophobic organic solvent of the organic phase containing the optically active carboxylic acid, thereby water-soluble components such as the enzyme or the buffer are removed. The same acid or base as described above can be also used to adjust the pH.

The amount of the hydrophobic organic solvent that may be used is normally from about 0.1 to about 200 parts by weight, preferably from about 0.2 to 100 parts by weight per one part by weight of the substrate. The extraction of the desired compound typically followed by phase separation may also be repeated, if necessary.

The isolated carboxylic acid may be further purified by column chromatography, recrystallization, or the like, if necessary.

The optically active N-protected-octahydro-1H-indole-2-carboxylic acid of formula (2) include the following compounds:
optically active N-tert-butoxycarbonyloctahydro-1H-indole-2-carboxylic acid,
optically active N-benzyloxycarbonyloctahydro-1H-indole-2-carboxylic acid,
optically active N-p-methoxybenzyloxycarbonyloctahydro-1H-indole-2-carboxylic acid,
optically active N-p-nitrobenzyloxycarbonyloctahydro-1H-indole-2-carboxylic acid,
optically active N-aryloxycarbonyloctahydro-1H-indole-2-carboxylic acid,
optically active N-9-fluorenylmethoxycarbonyloctahydro-1H-indole-2-carboxylic acid,
optically active N-acetyloctahydro-1H-indole-2-carboxylic acid,
optically active N-benzoyloctahydro-1H-indole-2-carboxylic acid,
optically active N-benzyloctahydro-1H-indole-2-carboxylic acid, and the like.

According to the present invention, a mixture of (2S, 3aS, 7aS) and (2R, 3aR, 7aR) N-protected-octahydro-1H-indole-2-carboxylate esters are asymmetrically hydrolyzed to give the optically active N-protected-octahydro-1H-indole-2-carboxylic acid of formula (2) having (2S, 3aS, 7aS) -configuration, and specific examples thereof include, for example, the optically active N-protected-octahydro-1H-indole-2-carboxylic acids exemplified above having the specific N-protecting groups as described above and a(2S, 3aS, 7aS)-configuration.

According to the present invention, the optically active N-protected-octahydro-1H-indole-2-carboxylate having (2R, 3aR, 7aR) configuration can also be obtained. Specific examples of the optically active N-protected-octahydro-1H-indole-2-carboxylic acid of formula (2) having a(2R, 3aR, 7aR) -configuration include, for example, those having the (2R, 3aR, 7aR)-configuration in place of the (2S, 3aS, 7aS) -configuration in the specific compounds exemplified above.

Optically active N-protected-octahydro-1H-indole-2-carboxylic acids of formula (2) produced in the present invention can be readily further converted to corresponding optically active octahydro-1H-indole-2-carboxylic acid by deprotecting, i.e. removal of the imino-protecting group represented by $R^2$ in a known manner or similar methods as disclosed in Protective Groups in Organic Synthesis, Greene, T. W. 3.sup.rd Edition, Wiley, the whole disclosure of which is incorporated herein by reference.

EXAMPLES

Hereinafter, the present invention will be set forth in detail with reference to Examples and the like; however, the present invention is by no means limited to these examples.

Reference Example 1

Production of a Mixture of Ethyl (2S, 3aS, 7aS)-octahydro-1H-indole-2-carboxylate and Ethyl (2R, 3aR, 7aR)-octahydro-1H-indole-2-carboxylate To a solution of 65.0 g (343.5 mmol) of an ethyl indole-2-carboxylate in 514 g of ethanol charged in an autoclave were added 38.3 g of concentrated sulfuric acid and then 5 g of 5% rhodium-carbon (in terms of dried weight). The atmosphere in the sealed autoclave was substituted with nitrogen and the autoclave was subsequently charged with hydrogen at 0.4 MPa and the temperature was raised to 60° C. While keeping the inside of autoclave at a pressure of 0.4 MPa, the solution was agitated at 60° C. for 10 hours. After completion of reaction, the catalyst was removed by filtration, and then the solvent was removed by distillation. The concentrated residue thus obtained was added to cooled water, and thereafter the resultant mixture mixed with a 10% aqueous potassium carbonate solution to adjust the pH of the mixture to 7. Further, after the solution was set to pH 9 with a 10% aqueous potassium bicarbonate solution, the water phase was extracted with diethyl ether. The organic phase thus obtained was washed with a 15% aqueous sodium chloride solution, and then dried over magnesium sulfate. Thereafter, the magnesium sulfate was removed by filtration, and the solvent in the solution thus obtained was removed by distillation to yield 57.2 g of a mixture of ethyl (2S, 3aS, 7aS)-octahydro-1H-indole-2-carboxylate and ethyl (2R, 3aR, 7aR)-octahydro-1H-indole-2-carboxylate [56.4 g of the desired compounds are contained, 285.8 mmol (yield 83.2%)].

Reference Example 2

Production of a Mixture of Ethyl (2S, 3aS, 7aS)-N-benzyloxycarbonyl-octahydro-1H-indole-2-carboxylate and Ethyl (2R, 3aR, 7aR)-N-benzyloxycarbonyl-octahydro-1H-indole-2-carboxylate In 38.8 g of ethyl acetate was dissolved 15.6 g (78.0 mmol) of the mixture of the enantiomers obtained in Reference Example 1. To the resulting solution were added 38.8 g of water and 15.5 g of potassium bicarbonate and mixed. To this solution cooled to 0° C. was dropped 15.0 g of benzyloxycarbonyl chloride over 1 hour. After the completion of dropping, the solution was raised to room temperature, and then agitated at room temperature for 4 hours to complete the reaction.

After the completion of reaction, to the reaction mixture was added 40 g of ethyl acetate to separate the resultant solution. From the resulting organic phase the solvent was removed by distillation to obtain an oily mixture of ethyl (2S, 3aS, 7aS)-N-benzyloxycarbonyl-octahydro-1H-indole-2-carboxylate and ethyl (2R, 3aR, 7aR)-N-benzyloxy-carbonyl-octahydro-1H-indole-2-carboxylate. This oily mixture was purified using n-hexane/ethyl acetate (eluate of the volume ratio of 85:15) by silica gel column chromatography to yield 24.3 g of a mixture of ethyl (2S, 3aS, 7aS)-N-benzyloxycarbonyl-octahydro-1H-indole-2-carboxylate and ethyl (2R, 3aR, 7aR)-N-benzyloxycarbonyl-octahydro-1H-indole-2-carboxylate [contained pure compounds were 22.8 g, 68.8 mmol (yield 88.2%)].

Example 1

Production of (2S, 3aS, 7aS)-N-benzyloxycarbonyl-octahydro-1H-indole-2-carboxylic Acid 15.1 g of dipotassium hydrogenphosphate were dissolved in 1000 g of water and then to the resulting solution was added phosphoric acid to prepare an aqueous buffer adjusted to pH 7.0.

2.5 ml of the aqueous buffer, 40.7 mg of the mixture obtained in Reference Example 2, and 101 mg of a culture containing Esterase 160A189Y363term derived from *Chromobacterium* SC-YM-1 strain (this strain was originally deposited in National Institute of Bioscience and Human-Technology Agency of Industrial Science and Techonology as an asccession No. FERMP-14009 by the applicant on Dec. 9, 1993 and at present continuously deposited as an accession No. FERMBP-6703 under Budapest Treaty) prepared in accordance with the method described in Japanese Unexamined Patent Application Publication No. 7-213280 were placed in a reaction vessel, and the resulting mixture was agitated at 30° C. for 20 hours. A solution prepared by adding 2.5 ml of acetone to the reaction solution after agitation was analyzed with a high performance liquid chromatogram (a column of CHIRALCEL OJ-RH, 4.6 mmf×15 cm, 5 mm available from Daicel Chemical Industries, Ltd. was used), and the resultant (2S, 3aS, 7aS)-N-benzyloxycarbonyloctahydro-1H-indole-2-carboxylic acid was analyzed and it was found that the yield was 48.2% and the enantiomer excess was 99.7% e. e. or more (other enantiomers were not detected.).

Example 2

Production of (2S, 3aS, 7aS)-N-benzyloxycarbonyl-octahydro-1H-indole-2-carboxylic Acid 13.3 g of dipotassium hydrogenphosphate was dissolved in 1.0 Kg of water and to the resulting solution was added 0.4 g of phosphoric acid to prepare an aqueous buffer adjusted to pH 8.0.

To this aqueous buffer were added 52.7 g (containing 51.2 g of pure compound, 154.5 mmol) of a racemic mixture obtained by the method as in Reference Example 2 and 50.7 g of a culture containing Esterase 160A189Y363term derived from *Chromobacterium* SC-YM-1 strain prepared in accordance with the method described in Japanese Unexamined Patent Application Publication No. 7-213280 and then the resulting mixture was agitated at 30° C. for 30 hours. During the reaction, 59.8 g of a 10% aqueous sodium carbonate solution was continuously added so that the solution was kept at pH 8.0. After the completion of reaction, the solution was adjusted to pH 2.2 by addition of 35% hydrochloric acid, and to this solution were added 25.4 g of celite and 150 g of ethyl acetate and then the resulting material was agitated for 0.5 hour. After insoluble matters were separated by filtering the suspension obtained by agitation, the filtrate solution thus obtained was adjusted to pH 10.5 using a 10% aqueous sodium hydroxide solution.

The resulting solution was separated into an oil phase and a water phase by phase separation.

To the water phase thus obtained was added 250 g of ethyl acetate and then extraction operation was carried out and separated into an oil phase and a water phase.

The oil phases thus obtained were combined and the resulting oil was dried over magnesium sulfate. Thereafter, the solvent was removed by distillation to yield 27.3 g of a colorless oily substance containing ethyl (2R, 3aR, 7aR)-N-benzyloxycarbonyloctahydro-1H-indole-2-carboxylate.

25.8 g (77.7 mmol) of ethyl N-benzyloxycarbonyl-octahydro-1H-indole-2-carboxylate were contained in this oily substance, thus the yield was 50.3% and the enantiomer excess was 96.5% e.e.

To the water phase separated previously from the oil phase was added 250 g of ethyl acetate. Then, to the aqueous solution was added 35% hydrochloric acid to make the pH of the solution 2.0, and subsequently the oil phase and the water phase were separated.

To the water phase thus obtained was added 250 g of ethyl acetate and the solution was subjected to extraction, and subsequently to phase separation. The oil phases thus obtained were combined and the resulting oil was dried over magnesium sulfate. Then, the solvent was removed by distillation to obtain 24.6 g of a colorless amorphous material containing 23.2 g (76.3 mmol) of pure (2S, 3aS, 7aS)-N-benzyloxy-carbonyloctahydro-1H-indole-2-carboxylic acid.

(2S, 3aS, 7aS)-N-benzyloxycarbonyloctahydro-1H-indole-2-carboxylic acid was obtained in a yield of 49.4% and with an enantiomer excess of 99.8% e.e or more. The other enantiomer was not detected.

Reference Example 3

Production of a Mixture of Ethyl (2S, 3aS, 7aS)-N-tert-butoxycarbonyl-octahydro-1H-indole-2-carboxylate and ethyl (2R, 3aR, 7aR)-N-tert-butoxycarbonyl-octahydro-1H-indole-2-carboxylate To a solution of 1.97 g (10.0 mmol) of the mixture of the enantiomers obtained in Reference Example 1 and 2.29 g of di-tert-butyldicarbonate in 9.9 g of toluene were added dropwise 1.11 g of triethylamine at 20° C. over 1 hour, and the solution was stirred for more than 12 hours at the temperature. Then the solution was washed with 1% hydrochloric acid, 5% sodium hydrogencarbonate and water. The separated oil phase was evaporated to give an oily mixture of ethyl (2S, 3aS, 7aS)-N-tert-butoxycarbonyl-octahydro-1H-indole-2-carboxylate and ethyl (2R, 3aR, 7aR)-N-tert-butoxycarbonyl-octahydro-1H-indole-2-carboxylate. This mixture was purified by silica gel column chromatography using an eluent of n-hexane/ethyl acetate(99/1, v/v) to obtain 2.77 g of mixture of ethyl (2S, 3aS, 7aS)-N-tert-butoxycarbonyl-octahydro-1H-indole-2-carboxylate and ethyl (2R, 3aR, 7aR)-N-tert-butoxycarbonyl-octahydro-1H-indole-2-carboxylate. (Yield 93.1%)

Example 3

Production of (2S, 3aS, 7aS)-N-tert-butyloxycarbonyl-octahydro-1H-indole-2-carboxylic Acid 0.29 g of dipotassium hydrogenphosphate was dissolved in 20.0 g of water and a buffer solution of which pH was adjusted to pH 8.0 by adding phosphoric acid thereto was prepared.

To this aqueous buffer were added 1.00 g (3.36 mmol) of the racemic mixture obtained by the method as in Reference Example 2 and 10.0 g of a culture containing Esterase 160A189Y363term derived from *Chromobacterium* SC-YM-1 strain prepared in accordance with the method described in Japanese Unexamined Patent Application Publication No. 7-213280 and then the resulting mixture was agitated at 30° C. for 40 hours. During the reaction, 1.8 g of a 10% aqueous sodium carbonate solution was continuously added so that the solution was kept at pH 8.0. After the completion of reaction, the solution was adjusted to pH 10.5 by addition of 10% sodium carbonate. Settled mixture was separated into oil phase and water phase, and the water phase was extracted with 10 go of ethyl acetate, settled and separated and the extraction was repeated again. The combined oil phase was dried over magnesium sulfate and evaporated to give 0.42 g of pale brown oily substance containing (2R, 3aR, 7aR)-N-tert-butyloxycarbonyl-octahydro-1H-indole-2-carboxylic acid. The oily substance contained 0.39 g (1.30 mmol) of (2R, 3aR, 7aR)-N-tert-butyloxycarbonyl-octahydro-1H-indole-2-carboxylic acid, and the yield was 38.7% and 99.3% ee (the enatiomer excess was measured by High Performance Liquid Chromatography using two pieces of CHIRALCEL OJ-RH, 4.6 mmø×15 cm, 5 mm manufactured by Daicel Company, Limited.) Other isomer was not detected.

To the water phase separated previously from the oil phase was added 30 g of ethyl acetate. Then, to the aqueous solution was added 10% hydrochloric acid to make the pH of the solution 2.8, and subsequently the oil phase and the water phase were separated.

To the water phase thus obtained was added 30 g of ethyl acetate and the solution was extracted and subjected to phase-separation, and the extraction was repeated again. The combined oil phase was dried over anhydrous magnesium sulfate and evaporated to give 0.46 g of pale brown oily substance containing 0.41 g of (2S, 3aS, 7aS)-N-tert-butyloxycarbonyl-octahydro-1H-indole-2-carboxylic acid. (2S, 3aS, 7aS)-N-tert-butyloxycarbonyl-octahydro-1H-indole-2-carboxylic acid was obtained in a yield of 45.4% and 99.5% ee or more. The other enantiomer was not detected (The enatiomer excess was measured by High Performance Liquid Chromatography using two pieces of CHIRALCEL OJ-RH, 4.6 mmø×15 cm, 5 mm manufactured by Daicel Company, Limited.)

---

SEQUENCE LISTING

<160> NUMBER OF SEQ ID NOS: 2

<210> SEQ ID NO 1
<211> LENGTH: 370
<212> TYPE: PRT
<213> ORGANISM: Chromobacterium SC-YM-1 (FERM BP-6703)

<400> SEQUENCE: 1

```
Met Thr Leu Phe Asp Gly Ile Thr Ser Arg Ile Val Asp Thr Asp Arg
                5                  10                  15

Leu Thr Val Asn Ile Leu Glu Arg Ala Ala Asp Asp Pro Gln Thr Pro
             20                  25                  30

Pro Asp Arg Thr Val Val Phe Val His Gly Asn Val Ser Ser Ala Leu
         35                  40                  45

Phe Trp Gln Glu Ile Met Gln Asp Leu Pro Ser Asp Leu Arg Ala Ile
     50                  55                  60

Ala Val Asp Leu Arg Gly Phe Gly Gly ser Glu His Ala Pro Val Asp
 65                  70                  75                  80

Ala Thr Arg Gly Val Arg Asp Phe Ser Asp Asp Leu His Ala Thr Leu
                 85                  90                  95

Glu Ala Leu Asp Ile Pro Val Ala His Leu Val Gly Trp Ser Met Gly
            100                 105                 110

Gly Gly Val Val Met Gln Tyr Ala Leu Asp His Pro Val Leu Ser Leu
        115                 120                 125

Thr Leu Gln Ser Pro Val Ser Pro Tyr Gly Phe Gly Gly Thr Arg Arg
    130                 135                 140

Asp Gly Ser Arg Leu Thr Asp Asp Ala Gly Cys Gly Gly Gly Gly
145                 150                 155                 160

Ala Asn Pro Asp Phe Ile Gln Arg Leu Ile Asp His Asp Thr Ser Asp
                165                 170                 175
```

```
Asp Ala Gln Thr Ser Pro Arg Ser Val Phe Arg Ala Gly Tyr Val Ala
            180                 185                 190

Ser Asp Tyr Thr Thr Asp His Glu Asp Val Trp Val Glu Ser Met Leu
        195                 200                 205

Thr Thr Ser Thr Ala Asp Gly Asn Tyr Pro Gly Asp Ala Val Pro Ser
    210                 215                 220

Asp Asn Trp Pro Gly Phe Ala Ala Gly Arg His Gly Val Leu Asn Thr
225                 230                 235                 240

Met Ala Pro Gln Tyr Phe Asp Val Ser Gly Ile Val Asp Leu Ala Glu
                245                 250                 255

Lys Pro Pro Ile Leu Trp Ile His Gly Thr Ala Asp Ala Ile Val Ser
            260                 265                 270

Asp Ala Ser Phe Tyr Asp Leu Asn Tyr Leu Gly Gln Leu Gly Ile Val
        275                 280                 285

Pro Gly Trp Pro Gly Glu Asp Val Ala Pro Ala Gln Glu Met Val Ser
    290                 295                 300

Gln Thr Arg Asp Val Leu Gly Arg Tyr Ala Ala Gly Gly Gly Thr Val
305                 310                 315                 320

Thr Glu Val Ala Val Glu Gly Ala Gly His Ser Ala His Leu Glu Arg
                325                 330                 335

Pro Ala Val Phe Arg His Ala Leu Leu Glu Ile Ile Gly Tyr Val Gly
            340                 345                 350

Ala Ala Ala Asp Pro Ala Pro Pro Thr Glu Ala Ile Ile Ile Arg Ser
        355                 360                 365

Ala Asp
    370

<210> SEQ ID NO 2
<211> LENGTH: 1110
<212> TYPE: DNA
<213> ORGANISM: Chromobacterium SC-YM-1 (FERM BP-6703)

<400> SEQUENCE: 2 atg act ctg ttc gat ggt atc act tcg cga atc gta gat act gat cgt      48
Met Thr Leu Phe Asp Gly Ile Thr Ser Arg Ile Val Asp Thr Asp Arg
                5                   10                  15 ctg act gtt aac atc ctg gaa cgt gcg gcc gac gac ccg cag acc ccg      96
Leu Thr Val Asn Ile Leu Glu Arg Ala Ala Asp Asp Pro Gln Thr Pro
            20                  25                  30 ccc gac cgc acg gtc gtg ttc gtc cac ggg aat gtg tcc tcc gcg ctg     144
Pro Asp Arg Thr Val Val Phe Val His Gly Asn Val Ser Ser Ala Leu
        35                  40                  45 ttc tgg cag gag atc atg cag gac ctg ccg agc gac ctg cgc gcc atc     192
Phe Trp Gln Glu Ile Met Gln Asp Leu Pro Ser Asp Leu Arg Ala Ile
    50                  55                  60 gcg gtc gac ctg cgc ggc ttc ggc ggc tcg gag cac gcg ccg gtc gac     240
Ala Val Asp Leu Arg Gly Phe Gly Gly ser Glu His Ala Pro Val Asp
65                  70                  75                  80 gcc acc cgc ggc gtc cgc gac ttc agc gac gat ctg cac gcg acc ctc     288
Ala Thr Arg Gly Val Arg Asp Phe Ser Asp Asp Leu His Ala Thr Leu
                85                  90                  95 gag gcg ctc gac atc ccg gtc gcg cat ctg gtc ggc tgg tcg atg ggc     336
Glu Ala Leu Asp Ile Pro Val Ala His Leu Val Gly Trp Ser Met Gly
            100                 105                 110 ggc ggc gtc gtc atg cag tat gcc ctc gac cac ccg gtg ctg agc ctg     384
Gly Gly Val Val Met Gln Tyr Ala Leu Asp His Pro Val Leu Ser Leu
        115                 120                 125
```

| | | |
|---|---|---|
| acc ctg cag tcg ccg gtg tcg ccc tac ggc ttc ggc ggc acc cgc cgt<br>Thr Leu Gln Ser Pro Val Ser Pro Tyr Gly Phe Gly Gly Thr Arg Arg<br>130                            135                        140 | | 432 |
| gac ggc tca cgc ctc acc gac gac gat gcc ggc tgc ggt ggc ggc ggt<br>Asp Gly Ser Arg Leu Thr Asp Asp Asp Ala Gly Cys Gly Gly Gly Gly<br>145                          150                        155                        160 | | 480 |
| gcg aac ccc gac ttc atc cag cgc ctc atc gac cac gac acc tcc gac<br>Ala Asn Pro Asp Phe Ile Gln Arg Leu Ile Asp His Asp Thr Ser Asp<br>                          165                        170                        175 | | 528 |
| gat gcg cag acc tcg ccc cgg agc gtc ttc cgc gcc ggc tac gtc gcc<br>Asp Ala Gln Thr Ser Pro Arg Ser Val Phe Arg Ala Gly Tyr Val Ala<br>                        180                        185                        190 | | 576 |
| tcg gac tac acc acc gac cac gag gac gtg tgg gtc gaa tcg atg ctc<br>Ser Asp Tyr Thr Thr Asp His Glu Asp Val Trp Val Glu Ser Met Leu<br>                        195                        200                        205 | | 624 |
| acc acg tcc acc gcc gac gga aac tac ccc ggc gat gcg gtg ccg agc<br>Thr Thr Ser Thr Ala Asp Gly Asn Tyr Pro Gly Asp Ala Val Pro Ser<br>210                            215                        220 | | 672 |
| gac aac tgg ccg ggc ttc gcc gcc ggc cgc cac ggc gtg ctg aac acc<br>Asp Asn Trp Pro Gly Phe Ala Ala Gly Arg His Gly Val Leu Asn Thr<br>225                            230                        235                        240 | | 720 |
| atg gcc ccg cag tac ttc gat gtg tcg ggg att gtc gac ctg gcc gag<br>Met Ala Pro Gln Tyr Phe Asp Val Ser Gly Ile Val Asp Leu Ala Glu<br>                        245                        250                        255 | | 768 |
| aag cct ccg atc ctg tgg atc cac ggc acc gcg gac gcg atc gtc tcc<br>Lys Pro Pro Ile Leu Trp Ile His Gly Thr Ala Asp Ala Ile Val Ser<br>                        260                        265                        270 | | 816 |
| gac gcg tcg ttc tac gac ctc aac tac ctc ggc cag ctg ggc atc gtc<br>Asp Ala Ser Phe Tyr Asp Leu Asn Tyr Leu Gly Gln Leu Gly Ile Val<br>                        275                        280                        285 | | 864 |
| ccc ggc tgg ccc ggc gaa gac gtc gcg ccc gcg cag gag atg gtg tcg<br>Pro Gly Trp Pro Gly Glu Asp Val Ala Pro Ala Gln Glu Met Val Ser<br>290                            295                        300 | | 912 |
| cag acc cgc gat gtc ctc ggc cgc tac gct gcg ggc ggc gga acg gtc<br>Gln Thr Arg Asp Val Leu Gly Arg Tyr Ala Ala Gly Gly Gly Thr Val<br>305                            310                        315                        320 | | 960 |
| acc gag gtc gcc gtc gag ggc gcg ggc cac tcc gcg cac ctg gag cgt<br>Thr Glu Val Ala Val Glu Gly Ala Gly His Ser Ala His Leu Glu Arg<br>                        325                        330                        335 | | 1008 |
| ccc gcg gtg ttc cgc cac gcg ctg ctc gag atc atc ggc tac gtc ggc<br>Pro Ala Val Phe Arg His Ala Leu Leu Glu Ile Ile Gly Tyr Val Gly<br>                        340                        345                        350 | | 1056 |
| gcg gcg gcc gac ccc gcc ccg ccg acc gag gcg atc atc atc cgc tcc<br>Ala Ala Ala Asp Pro Ala Pro Pro Thr Glu Ala Ile Ile Ile Arg Ser<br>                        355                        360                        365 | | 1104 |
| gcc gac<br>Ala Asp<br>        370 | | 1110 |

What is claimed is:

1. A process for producing an optically active N-protected-octahydro-1H-indole-2-carboxylic acid of formula (2):

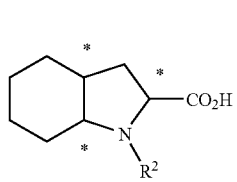
(2)

wherein $R^2$ represents a protecting group of an imino group, and the carbon atoms denoted with asterisks (*) represent asymmetric carbon atoms, which process comprises reacting a mixture of enantiomers of N-protected-octahydro-1H-indole-2-carboxylate of formula (1):

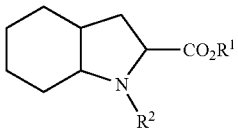
(1)

wherein $R^1$ is a C1-4 alkyl group, and $R^2$ is as defined above, with an enzyme capable of asymmetrically hydrolyzing the —$CO_2R^1$ group of formula (1), wherein the enzyme is an enzyme
i) produced by a microorganism deposited with accession number FERM BP-6703,
ii) comprising a polypeptide sequence of SEQ ID NO:1, or
iii) comprising a polypeptide sequence of SEQ ID NO:1 modified by deletion, substitution or both of the amino acids selected from the group consisting of amino acid 160 of SEQ ID NO:1 and amino acid 189 of SEQ ID NO:1.

2. A process according to claim 1, wherein the mixture of enantiomers of N-protected-octahydro-1H-indole-2-carboxylate of formula (1) is a mixture of a single enantiomer and an antipode thereof.

3. A process according to claim 2, wherein the single enantiomer and antipode thereof are the compound of formula (1') and the compound of formula (1"):

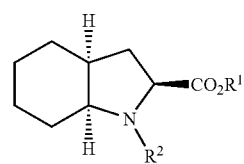
(1')

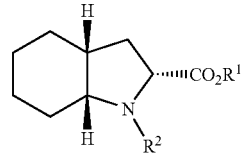
(1")

wherein $R^1$ is and $R^2$ are as defined in claim 1.

4. A process according to claim 2, which further comprises isolating the antipode of the resulting asymmetrically hydrolyzed optically active N-protected-octahydro-1H-indole-2-carboxylic acid as an ester, and hydrolyzing the isolated optically active N-protected-octahydro-1H-indole-2-carboxylic acid ester to produce an antipode acid compound of the enantiomer of formula (2).

5. A process according to claim 4, wherein the hydrolyzing of the N-protected-octahydro-1H-indole-2-carboxylate is conducted in the presence of an alkali.

6. A process according to claim 1, wherein $R^2$ is a tert-butoxycarbonyl group, a benzyloxycarbonyl group, an acetyl group, a benzoyl group or a benzyl group.

7. A process according to claim 6, wherein $R^2$ is a benzyloxycarbonyl group.

8. A process according to claim 1, wherein $R^1$ is ethyl.

9. A process according to claim 1, which further comprises the step of deprotecting the optically active N-protected-octahydro-1H-indole-2-carboxylic acid of formula (2) to produce corresponding optically active octahydro-1H-indole-2-carboxylic acid.

* * * * *

UNITED STATES PATENT AND TRADEMARK OFFICE
CERTIFICATE OF CORRECTION

| | | |
|---|---|---|
| PATENT NO. | : 7,439,036 B2 | Page 1 of 1 |
| APPLICATION NO. | : 10/975076 | |
| DATED | : October 21, 2008 | |
| INVENTOR(S) | : Hirata | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 617 days.

Signed and Sealed this

Twenty-eighth Day of September, 2010

David J. Kappos
*Director of the United States Patent and Trademark Office*